US00PP19421P2

(12) United States Plant Patent
Takahata et al.

(10) Patent No.: US PP19,421 P2
(45) Date of Patent: Nov. 4, 2008

(54) ***IPOMOEA* PLANT NAMED 'KYUIKUKAN 3'**

(50) Latin Name: *Ipomoea batatas*
Varietal Denomination: Kyuikukan 3

(75) Inventors: Yasuhiro Takahata, Miyakonojo (JP); Hiroki Nakayama, Miyakonojo (JP); Yoshinori Nakazawa, Kumamoto (JP); Masaru Yoshinaga, Miyakonojo (JP); Masaru Tanaka, Miyakonojo (JP); Toru Kumagai, Tsukuba (JP); Yumi Kai, Miyakonojo (JP); Tetsufumi Sakai, Miyakonojo (JP); Kazunari Iwaki, Kanagawa (JP); Kenji Katayama, Miyakonojo (JP); Yasuyuki Murakami, Shiga (JP)

(73) Assignee: Suntory Flowers Ltd, Tokyo (JP)

( * ) Notice: Subject to any disclaimer, the term of this patent is extended or adjusted under 35 U.S.C. 154(b) by 0 days.

(21) Appl. No.: 11/800,767

(22) Filed: May 7, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—C. A. Whealy

(57) ABSTRACT

A new and distinct cultivar of *Ipomoea* plant named 'Kyuikukan 3', characterized by its compact and outwardly trailing growth habit; and bright green-colored foliage.

1 Drawing Sheet

Botanical designation: *Ipomoea batatas.*
Cultivar denomination: 'Kyuikukan 3'.

BACKGROUND OF THE INVENTION

The present invention relates to a new and distinct cultivar of *Ipomoea,* botanically known as *Ipomoea batatas,* and hereinafter referred to by the name 'Kyuikukan 3'.

The new *Ipomoea* is a product of a planned breeding program conducted by the Inventors in Miyazaki, Japan. The objective of the breeding program is to create new compact *Ipomoea* cultivars with attractive foliage shape and coloration.

The new cultivar originated from a cross-pollination made by the Inventors in June, 2001 of the *Ipomoea batatas* cultivar Sweet Garden, not patented, as the female, or seed, parent with the *Ipomoea batatas* cultivar Sweet Line, not patented, as the male, or pollen, parent. The cultivar Kyuikukan 3 was discovered and selected by the Inventors as a single plant within the progeny of the stated cross-pollination in a controlled environment in Miyazaki, Japan.

Asexual reproduction of the new *Ipomoea* by terminal cuttings in a controlled environment in Miyazaki, Japan since December, 2005, has shown that the unique features of this new *Ipomoea* are stable and reproduced true to type in successive generations.

SUMMARY OF THE INVENTION

The cultivar Kyuikukan 3 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kyuikukan 3'. These characteristics in combination distinguish 'Kyuikukan 3' as a new and distinct cultivar of *Ipomoea:*

1. Compact and outwardly trailing growth habit.
2. Bright green-colored tri-lobed foliage.

Plants of the new *Ipomoea* can be compared to plants of the female parent, the cultivar Sweet Garden. Plants of the new *Ipomoea* differ from plants of the cultivar Sweet Garden in the following characteristics:

1. Plants of the new *Ipomoea* have longer internodes than plants of the cultivar Sweet Garden.
2. Plants of the new *Ipomoea* and the cultivar Sweet Garden differ in leaf coloration.

Plants of the new *Ipomoea* can be compared to plants of the male parent, the cultivar Sweet Line. Plants of the new *Ipomoea* differ from plants of the cultivar Sweet Line in the following characteristics:

1. Plants of the new *Ipomoea* are more compact and more trailing than plants of the cultivar Sweet Line.
2. Plants of the new *Ipomoea* and the cultivar Sweet Line differ in leaf shape.

Plants of the new *Ipomoea* can be compared to plants of the *Ipomoea batatas* cultivar Sweet Caroline Light Green, disclosed in U.S. Plant Pat. No. 15,028. In side-by-side comparisons conducted in Shiga, Japan, plants of the new *Ipomoea* differed from plants of the cultivar Sweet Caroline Light Green in the following characteristics:

1. Plants of the new *Ipomoea* were shorter than plants of the cultivar Sweet Caroline Light Green.
2. Plants of the new *Ipomoea* had longer internodes than plants of the cultivars Sweet Caroline Light Green.
3. Plants of the new *Ipomoea* had smaller leaves and shorter petioles than plants of the cultivar Sweet Caroline Light Green.
4. Plants of the new *Ipomoea* and the cultivar Sweet Caroline Light Green differed in leaf shape and leaf color.

BRIEF DESCRIPTION OF THE PHOTOGRAPHS

The accompanying colored photographs illustrate the overall appearance of the new *Ipomoea,* showing the colors as true as it is reasonably possible to obtain in colored reproductions of this type. Colors in the photographs may differ slightly from the color values cited in the detailed botanical description which accurately describe the colors of the new *Ipomoea*.

The photograph at the top of the sheet comprises a side perspective view of a typical plant of 'Kyuikukan 3' grown in a container.

The photograph at the bottom of the sheet comprises a close-up view of typical leaves of 'Kyuikukan 3'.

DETAILED BOTANICAL DESCRIPTION

The photographs and following observations, measurements and values describe plants grown in Shiga, Japan in a polyethylene-covered greenhouse during the summer under conditions which closely approximate commercial production. During the production of the plants, day temperatures were about 28° C. and night temperatures were about 18° C. Plants were about four months old when the photographs and the description were taken. In the detailed description, color references are made to The Royal Horticultural Society Colour Chart, 2001 Edition, except where general terms of ordinary dictionary significance are used.

Botanical classification: *Ipomoea batatas* cultivar Kyuikukan 3.

Parentage:

*Female, or seed, parent.*—*Ipomoea batatas* cultivar Sweet Garden, not patented.

*Male, or pollen, parent.*—*Ipomoea batatas* cultivar Sweet Line, not patented.

Propagation:

*Type.*—By terminal cuttings.

*Time to initiate roots.*—About three days at temperatures of 20° C. to 25° C.

*Time to produce a rooted young plant.*—About four weeks at temperatures of 20° C. to 25° C.

*Root description.*—Thick, fleshy. Development of tubers, ellipsoidal in shape and red in color, has been observed.

Plant description:

*Plant habit.*—Compact and outwardly trailing plant habit. Freely branching habit; pinching enhances lateral branch development; vigorous growth habit.

*Plant height.*—About 10.8 cm.

*Plant diameter.*—About 49 cm.

Lateral branch description:

*Length.*—About 11 cm.

*Diameter.*—About 3.3 mm.

*Internode length.*—About 2.3 cm.

*Strength.*—Strong.

*Texture.*—Pubescent.

*Color.*—145C.

Foliage description:

*Arrangement.*—Alternate, simple.

*Length.*—About 9.8 cm.

*Width.*—About 8.5 cm.

*Shape.*—Roughly palmate.

*Apex.*—Acute.

*Base.*—Cordate.

*Margin.*—Entire; deeply lobed.

*Texture, upper and lower surfaces.*—Sparsely pubescent.

*Venation pattern.*—Palmate.

*Color.*—Developing and fully expanded foliage, upper surface: 144B; venation, 145D. Developing and fully expanded foliage, lower surface: 146D; venation, 145D.

*Petiole.*—Length: About 5.4 cm. Diameter: About 2.3 mm. Texture, upper and lower surfaces: Sparsely pubescent. Color, upper and lower surfaces: 145B.

Flower description:

Plants of the new *Ipomoea* do not develop flowers.

Temperature tolerance: Plants of the new *Ipomoea* have been observed to tolerate temperatures from about 5° C. to about 35° C.

Pathogen/pest resistance: Plants of the new *Ipomoea* have not been observed to be resistant to pests and pathogens common to *Ipomoea*.

It is claimed:

1. A new and distinct *Ipomoea* plant named 'Kyuikukan 3' as illustrated and described.

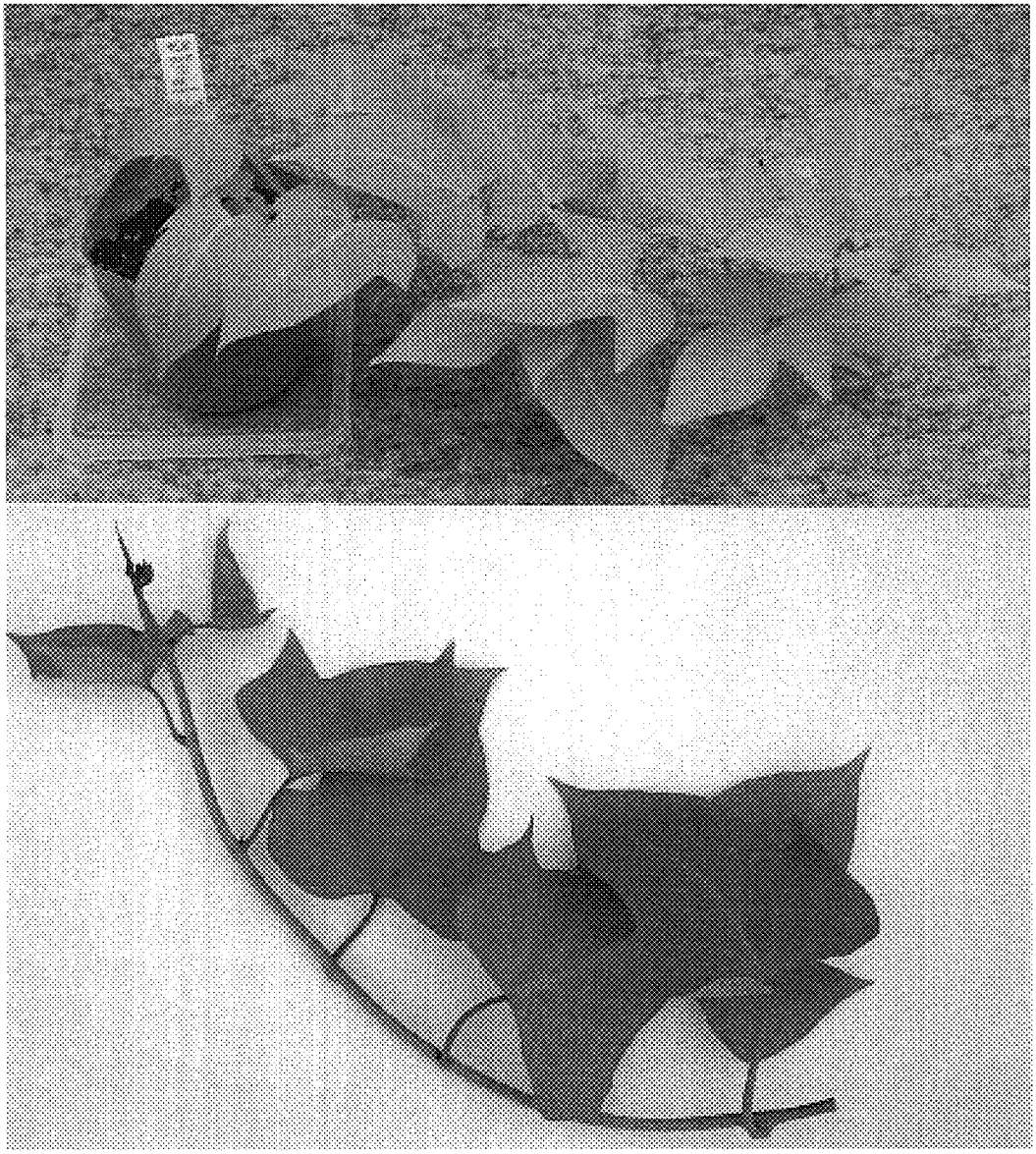

* * * * *